2 Sheets--Sheet 1.

J. J. JOHNSTON.

Processes and Apparatus for Evaporating Liquids.

No. 5,570.

Reissued September 9, 1873.

Attest;
Edw. M. Down
Alonzo Hughes

Inventor:
James J. Johnston

2 Sheets--Sheet 2.

J. J. JOHNSTON.

Processes and Apparatus for Evaporating Liquids.

No. 5,570. Reissued September 9, 1873.

Attest;
Edw. W. Donn
Alonzo Hughes

Inventor;
James J. Johnston

UNITED STATES PATENT OFFICE.

JAMES J. JOHNSTON, OF COLUMBIANA, OHIO, ASSIGNOR OF PART INTEREST TO JOHN CAMPBELL AND CHARLES SEIBERT, OF ALLEGHENY, PA.

IMPROVEMENT IN THE PROCESSES AND APPARATUS FOR EVAPORATING LIQUIDS.

Specification forming part of Letters Patent No. 50,935, dated November 14, 1865; antedated November 2, 1865; reissue No. 5,570, dated September 9, 1873; application filed September 3, 1873.

*To all whom it may concern:*

Be it known that I, JAMES J. JOHNSTON, formerly of the city and county of Allegheny, in the State of Pennsylvania, and now of Columbiana, in the county of Columbiana and State of Ohio, have invented a certain new and useful Improvement in Process and Apparatus for Evaporating and Vaporizing Liquids; and I do hereby declare that the following is a full, clear, and exact description thereof, reference being had to the accompanying drawings and to the letters of reference marked thereon.

The nature of my invention consists in combining atmospheric air and steam, which compound is superheated and brought in direct contact or commingled with liquids for the purpose of evaporating and vaporizing them.

To enable others skilled in the art to which it is most nearly connected to make and use my invention, I will proceed to describe an apparatus adapted to my process for evaporating and vaporizing liquids.

Figure 1:
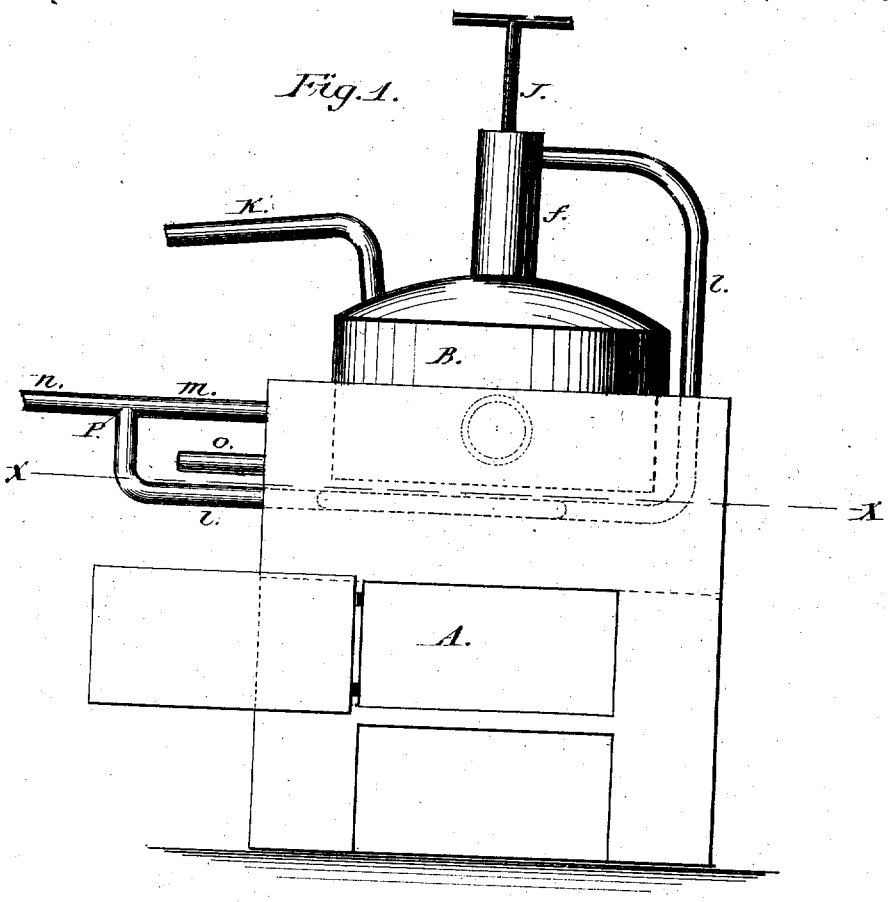
Figure 2:
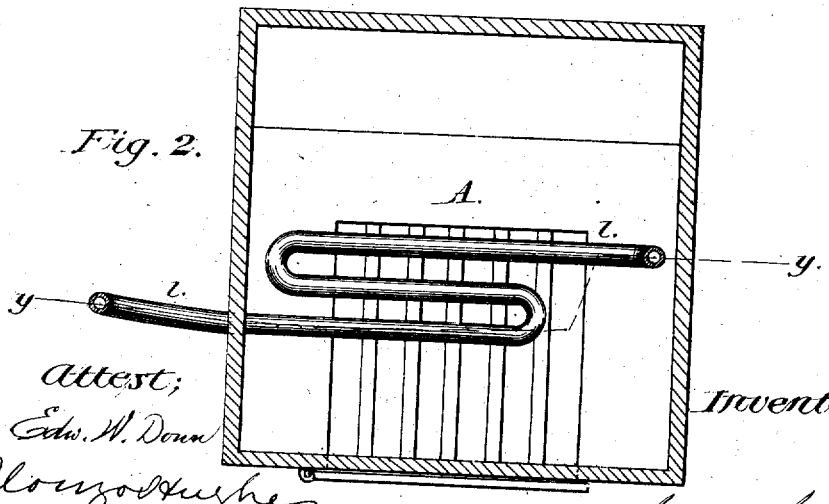
Figure 3:
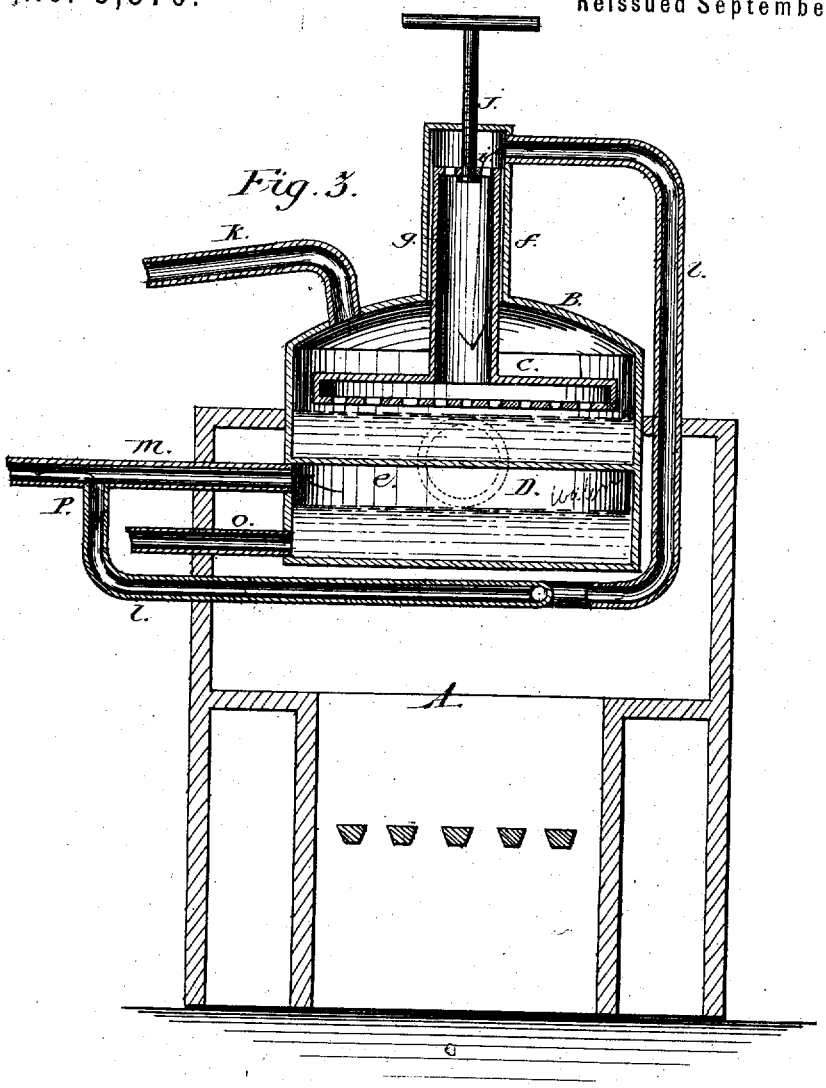

In the accompanying drawings, which form part of my specification, Figure 1 is a front elevation of the apparatus used in my process for evaporating and vaporizing liquids. Fig. 2 is a horizontal section of the same at line *x* of Fig. 1. Fig. 3 is a vertical section of the apparatus at line *y* of Fig. 2.

In the accompanying drawings, A represents the furnace. B represents the still or retort, which is divided into two compartments, C and D, by means of a partition, *e*. The compartment C is furnished with a hollow column, *f*, into the bore of which is fitted another column, *g*, on the lower end of which is a hollow disk, *h*, the lower face of which is perforated with a large number of small openings, and in the upper end of the column *g* are a number of openings, *i*. The column *g* and its disk *h* are suspended in the column *f* and still C through the medium of a screw, J, whereby they can be raised or lowered in the still, so that the disk may be just above the liquid therein, or lowered below its surface to any desired point. To the crown of the still or retort is a pipe, *k*, for the purpose of carrying off the vapor evolved from the liquid in the still. To the upper end of the column *f* is attached a pipe, *l*, which passes down into the furnace A, and, traversing back and forward under the still, passes out of the furnace, and is connected to the pipe *m* communicating with the upper portion of the compartment D of the still or retort. Near the bottom of the compartment D is a pipe, *o*, communicating with a water-supply. To the branch *n* of the pipe *m* should be attached an air-blast device.

From the foregoing description, and by reference to the accompanying drawings, the skillful mechanic will readily understand the construction and arrangement of the device herein shown and described for evaporating and vaporizing liquids; but I wish it clearly understood that I do not confine myself to any particular construction of the various parts herein described and shown, for they may be varied without departing from the principle of my process for evaporating and vaporizing liquids by commingling therewith superheated steam and air combined. The branch *n* of the pipe *m* may communicate with a steam-engine for the purpose of operating it. The compartment A being supplied with water, and the compartment C with the liquid to be evaporated and vaporized, fire is made in the furnace, which will generate steam in the compartment D, which will heat the liquid in the compartment C, and as soon as a sufficient pressure of steam is generated it will pass through the pipe *m*, and, the air-blast device being put in operation, the steam and air will combine at the point P, and, entering the pipe *l*, will pass through it and enter the column *f*, and pass through the openings *i* into the column *g*, and down into the disk *h*, and out through the small openings therein, and, acting on the surface of the heated liquid, will rapidly evaporate and vaporize it, and the air and steam combined and superheated, having performed its office on or in the liquid in the compartment C, will commingle with the vapor and pass off through the pipe *k*.

The application of my process and apparatus for evaporating and vaporizing liquids, and its adaptation to the arts, I leave to the judgment and skill of the mechanic, who will readily understand that it is applicable to any manufacture where it is necessary to evaporate and vaporize a liquid or liquids connected therewith.

Having thus described my improvement, what I claim as of my invention is—

1. The process herein described for evaporating and vaporizing liquids, viz., by the application or contact of superheated steam and air combined.

2. The combination of the furnace A, still B, adjustable disk *h*, and pipes *k*, *l*, and *m*, substantially as herein described, and for the purpose set forth.

JAMES J. JOHNSTON.

Witnesses:
W. I. COLLAMER,
JNO. D. PATTEN.